United States Patent [19]

Mausner et al.

[11] 4,054,541

[45] Oct. 18, 1977

[54] SPRAY DRIED ALCOHOL ETHER SULFATE DETERGENT COMPOSITIONS

[75] Inventors: Marvin L. Mausner, Teaneck; Albert Benson, Fair Lawn, both of N.J.

[73] Assignee: Witco Chemical Corporation, New York, N.Y.

[21] Appl. No.: 742,942

[22] Filed: Nov. 18, 1976

Related U.S. Application Data

[63] Continuation of Ser. No. 520,588, Nov. 4, 1974, abandoned.

[51] Int. Cl.$^2$ .................. A61K 7/50; C11D 1/29; C11D 3/60; C11D 17/06
[52] U.S. Cl. ............................ 252/532; 252/89 R; 252/133; 252/174; 252/551; 252/DIG. 5
[58] Field of Search ............... 252/133, 532, 551, 174, 252/DIG. 5, 135, 89

[56] References Cited

U.S. PATENT DOCUMENTS

| | | | |
|---|---|---|---|
| 2,766,212 | 10/1956 | Grifo | 252/551 |
| 3,414,520 | 12/1968 | McDonnell | 252/110 |
| 3,658,727 | 4/1972 | Mast | 252/538 |
| 3,776,861 | 12/1973 | Mausner et al. | 252/545 |
| 3,793,233 | 2/1974 | Rose | 252/547 |
| 3,801,511 | 4/1974 | Lemoff | 252/135 |
| 3,849,346 | 11/1974 | Kuwamura | 252/531 |

OTHER PUBLICATIONS

McCutcheon's Detergents & Emulsifiers - 1972 Annual, published by McCutcheon'Division, Allured Publishing Co., Ridgewood, N.J. 1972.

*Primary Examiner*—Dennis L. Albrecht
*Attorney, Agent, or Firm*—Albert L. Gazzola; Morton Friedman

[57] ABSTRACT

Dry powder compositions in the form of spray dried beads comprising an alcohol ether sulfate, magnesium sulfate and a buffer are found particularly suitable for providing a substantially dust-free and Ph stable bubblebath formulation.

7 Claims, No Drawings

SPRAY DRIED ALCOHOL ETHER SULFATE DETERGENT COMPOSITIONS

This is a continuation, of application Ser. No. 520,588, filed Nov. 4, 1974, now abandoned.

This invention relates to an improved bubblebath formulation in dry powder form. More particularly this invention relates to an alcohol ether sulfate composition in the form of spray-dried beads particularly suitable for use as a bubblebath formulation.

Considerable difficulty is encountered during the formulation of commercially acceptable alcohol ether sulfate based dry powder detergent compositions. More specifically, the adaptation of the conventional spray-drying methods of manufacture to substantially neutral compositions wherein significant amounts of alcohol ether sulfate are present, i.e., 7-8% and more, has not been readily accomplished heretofor. Previous attempts to spray dry slurries containing significant proportions of an alcohol ether sulfate product have resulted in serious difficulties with regard to tackiness of the finished product. It is important that commercially acceptable spray-dried beads retain the form of a hollow, spherical bead, this form being important for a fast dissolving product. Moreover, for compositions such as bubblebaths which contain amounts of active ingredient of about 7-20%, for instance, spray drying is a desirable economical method of production.

The present invention discloses a detergent composition which is particularly amenable to the spray-drying process and with the further provision of forming spray-dried beads.

It is an object of this invention to provide a composition for forming spray-dried beads suitable in a bubblebath formulation, which beads are substantially dust free, low in density and which will withstand packaging and transport without breaking down.

It is further an object of this invention to provide a spray-dried alcohol ether sulfate detergent product which will remain pH stable during spray drying and for long periods under normal conditions of storage and transport.

It is a further object of this invention to provide a composition having a neutral pH, i.e., pH of between 6.0-8.0, which lends itself to rapid spray drying at high temperatures, i.e., about 700° F, without decomposition.

It is a further object of this invention to provide a method of spray drying slurries containing significant proportions of an alcohol ether sulfate to form hollow spherical beads which are substantially dust-free.

Another object of the invention is to provide a method of spray drying slurries containing significant proportions of an alcohol ether sulfate which will result in the formation of beads with properties that are particularly suitable for use as bubblebath compositions.

Other objects of the invention will be apparent from the following detailed descriptions.

In accordance with the present invention there is provided dry powder detergent compositions in the form of spray-dried beads which comprise an alcohol ether sulfate, hydrate forming salt and a buffer.

The aforesaid beads are prepared quite readily by conventional spray drying techniques. The compositions of the present invention are in the form of hollow, spherical beads which retain their physical form, are free-flowing, have suppressed dusting tendencies, exhibit good foaming characteristics for use as a bubblebath formulation, and have a bulk density within a commercially acceptable range.

The alcohol ether sulfates employed in the composition of the present invention may be described as having the general formula $RO(CH_2CH_2O)_x$—$SO_3$—M wherein R is an alkyl chain having from about 10 to 18 carbon atoms, $x$ is an integer from about 2 to 6 and M is a cation.

The alcohol ether sulfates can be made by the condensation, by known methods, of ethylene oxides on the monohydric alcohols having 10 to 18 carbon atoms. Preferably, R has 12 to 15 carbon atoms. The alcohols may be derived from fats, e.g., coconut oil, or they may be synthetic. Lauryl alcohol and straight chain alcohols derived from coconut oil are preferred. Such alcohols are reacted with 2 to 6, and especially 3 to 5 molar proportions of ethylene oxide and the resulting mixture of molecular species, having, for example, an average of 3 moles of ethylene oxide per mole of alcohol, is sulfated and neutralized.

The cation M may be alkali metal, ammonium, substituted ammonium radical, alkaline earth metal, or a mixture of any two or more of these. The aforesaid alcohol ether sulfates are employed in amounts ranging from about 5 to 12% by weight of the overall composition and preferably in the range of about 7 to 9% by weight of product. For optimum results, it has been found that the aforesaid sulfated surfactant should be derived from alkanols having from 12 to 15 carbon atoms or mixtures of such alkanols, the degree of ethoxylation should be in the range of about 3 to 5 mols of ethylene oxide per mol of alkanol, and the alcohol ether sulfate should preferably be employed in the form of the sodium salt.

The second component of the composition is a hydrate forming salt and preferably one such as magnesium sulfate. The magnesium sulfates useful in these compositions may take the form of any of the commercial grades of magnesium sulfate, such as epsom salts or magnesium sulfate heptahydrate. The magnesium sulfate is present in an amount of from about 5 to 15% of the total composition and preferably at about the 10% level.

The third component of the composition is a buffer. The buffer is employed for the purpose of preventing acid catalyzed decomposition. The buffer acts to insure stability by adjusting the pH of a 5% by weight solution to a value between 6 and 8. Preferred buffers include the salts of citric, maleic or phosphoric acid as well as mixtures of these salts. The buffer is present in an amount of from about 0.25 to 2.5% of the total composition and preferably at the 1.5% level.

A particularly preferred buffer is a combined buffer system of about 0.5% by weight of a citrate and about 1.0% by weight of a phosphate. Particularly suitable is a combination as aforesaid of disodium phosphate and trisodium citrate. This citrate-phosphate buffer system provides a stable pH of between about 6.0 and 7.0 over long periods of time of about 4 months or more.

While the essential principal ingredient is an alcohol ether sulfate, small percentages of additional detergents may also be employed providing they do not impair the performance of the aforesaid combination of alcohol ether sulfate, magnesium sulfate and buffer.

Additionally the compositions of the present invention may contain a water-soluble starch hydrolysate which is a starch carbohydrate which has been subjected to acid or enzyme (amylase, e.g.) catalyzed hydrolysis. These materials are utilized within the range of 1 to 3% by weight of the composition. These hydrolysates, which are employed preferably at about the 2% level, are characterized as having a dextrose equivalent between about 15 and 44. Particularly preferred are corn starch hydrolysates which have a dextrose equivalent of 15 to 20. The starches may also be derived from sources such as wheat, rice, potato and the like. These water-soluble starch hydrolysates are composed mainly of higher polysaccharides but significant proportions of di- to hexasaccharides are also present.

The compositions of the present invention may also contain sodium chloride which is used generally in the 8 to 12% range and preferably at the 10% level.

A further ingredient which may be present is a sodium or potassium sulfate filler, such as sodium sulfate and the like. The exact amount will, of course, be dependent on the quantities of other components used. Generally speaking, the amount will vary over the 40 to 60% range and preferably within the range of 50 to 55% by weight.

The compositions of the present invention may contain other ingredients useful in dry powder detergent compositions, such as perfumes, coloring agents, bacteriocides, sequestering agents and the like. Such additives may be incorporated either before or after the spray drying is carried out.

The composition as aforesaid is formed into a slurry, and the slurry is then forced through spray nozzles into towers wherein the small liquid particulates are dried as they contact a stream or vortex of heated air. The composition is produced thereby in the form of hollow, thinwalled spheres or beads having a low apparent bulk density of about 0.20 to 0.25 gram per cc., and characterized by excellent solubility, good foaming properties, uniformity of particles which are essentially nontacky, dust-free and therefore provide a product with good packaging properties as well as being particularly suitable for use as bubblebath formulations.

The spray drying conditions are somewhat variable and generally air inlet temperatures of 700° to 840° F and air outlet temperatures of 200° to 260° F are used. The pressure at which the slurry is pumped to the spray nozzles may be in the range of 250 to 600 p.s.i.g. The slurry concentration will be from 40 to 70% by weight with a concentration of about 50% by weight solids producing the best viscosity.

The invention is further illustrated by the following examples which are not to be considered as limitative of its scope. All percentages are by weight or as otherwise indicated.

EXAMPLES 1-2

Spray dried bubblebath compositions were prepared having the following compositions:

| Component | 1 | 2 |
|---|---|---|
| Alcohol ether sulfate[1] | 7.5% | 8.0% |
| MgSO$_4$[8] | 10.0% | 10.0% |
| Disodium Phosphate | 1.0% | 1.0% |
| Trisodium Citrate | 0.5% | 0.5% |
| Modified Starch[2] | 2.0% | 2.0% |
| NaCl | 10.0% | 10.0% |
| Na$_2$SO$_4$[3] | R[7] | R[7] |
| Water | 2.0% | 2.0% |
| Surfactant[4] | 0.2% | 0.2% |
| Perfume[5] | 0.15% | 0.10% |
| CDA[6] | 0.5% | — | notes:
[1] sodium salt, mixture of $C_{12}$ to $C_{15}$ linear monohydric alkanols containing 4 moles of ethylene oxide per mole of alkanol
[2] mixture of mono-, di-, and polysaccharides
[3] filler
[4] ethoxylated coconut fatty acid monoethanolamide having 5 ethoxy groups
[5] Florasynth 1768-1 (Fragrance)
[6] coconut diethanolamide
[7] remainder
[8] heptahydrate, weight on anhydrous basis The aforesaid compositions were prepared by spray drying from a slurry having a concentration of from 50 to 55% solids which was pumped at a pressure of from 250 to 350 psig. The spray dry tower air inlet temperature was 750° F. The product produced was a free-flowing, essentially dust-free product having less than 0.5% by weight through 200 mesh. Any minimal dust settled rapidly. The pH of the product at packaging was 6.9 - 7.0 and remained stable over a period of about 4 months.

Compositions similar to those of Examples 1 and 2 but having 5.0% and 15.0% magnesium sulfate also provide acceptable spray dried products.

EXAMPLES 3-7

For comparative purposes, spray dried compositions are prepared with other detergent materials and having the following ranges of proportions. Spray drying conditions are similar to those of the aforesaid Examples. Comments are given below with regard to the properties of each of the spray dried products produced.

| Component | 3 | 4 | 5 | 6 | 7 |
|---|---|---|---|---|---|
| (a) | 15% | 10% | 15% | 10% | 2% |
| (b) | 5% | 5% | none | 2% | 2% |
| (c) | 5% | 5% | 10% | 2% | none |
| (d) | none | none | 15% | 5% | 20% |
| (e) | 15% | 15% | none | 10% | 10% |
| (f) | 60% | 65% | 60% | 73% | 66% | notes:
(a) Sodium $C_{14}$-$C_{16}$ alpha-olefin sulfonate
(b) Sodium n-dodecyl benzene sulfonate
(c) Water soluble corn starch hydrolysate having a dextrose equivalent of 15-20
(d) Magnesium sulfate heptahydrate
(e) Sodium Chloride
(f) Sodium Sulfate

EXAMPLE 3

A relatively high density product, about 0.3 g/cc is produced and the bead is too fragile for packaging operations.

EXAMPLE 4

An extremely dusty product is obtained with wide variations in density.

EXAMPLE 5

Again the product dusts excessively.

EXAMPLE 6

A very high density product, 0.4 - 0.5 g/cc. is obtained which dusts excessively.

EXAMPLE 7

The product is extremely dusty.

Although the present invention has been described with reference to particular embodiments and examples, it will be apparent to those skilled in the art that variations and modifications of this invention can be made and that equivalents can be substituted therefor without departing from the principles and true spirit of the invention.

What is claimed is:

1. A spray dried hollow bead detergent composition comprising, by weight, about 5–12% of an alcohol ether sulfate; about 5–15% of magnesium sulfate; and 0.25–2.5% of a buffer selected from the group consisting of the salts of citric, maleic and phosphoric acid, and mixtures thereof; about 8–12% of sodium chloride and about 40–60% of a sodium or potassium sulfate filler, wherein an alkyl chain in the alcohol ether sulfate has from about 10 to 18 carbon atoms and wherein the alcohol ether sulfate has from about 3 to 7 ether groups.

2. The composition of claim 1, wherein said hydrate forming salt is magnesium sulfate.

3. The composition of claim 1, wherein said buffer comprises at least one of a citric acid salt, a maleic acid salt, and a phosphoric acid salt.

4. The composition of claim 3, wherein said buffer comprises a mixture of about 0.5% of a citric acid salt and about 1.0% of a phosphoric acid salt.

5. The composition of claim 4, wherein said buffer comprises disodium phosphate and trisodium citrate.

6. The composition of claim 1, wherein an alkyl chain in the alcohol ether sulfate has from about 12 to 15 carbon atoms.

7. A method for forming a hollow bead detergent composition comprising spray drying a composition comprising by weight, about 5–12% of an alcohol ether sulfate, about 5–15% of magnesium sulfate, and about 0.25–2.5% of a buffer selected from the group consisting of the salts of citric, maleic and phosphoric acid, and mixtures thereof; about 8–12% of sodium chloride, and about 40–60% of a sodium or potassium sulfate filler, wherein an alkyl chain in the alcohol ether sulfate has from about 10 to 18 carbon atoms and wherein the alcohol ether sulfate has from about 3 to 7 ether groups.

* * * * *